United States Patent [19]

Hitzman

[11] 4,261,420
[45] Apr. 14, 1981

[54] ENRICHED OIL RECOVERY USING CARBON DIOXIDE

[75] Inventor: Donald O. Hitzman, Bartlesville, Okla.

[73] Assignee: Provesta Corporation, Bartlesville, Okla.

[21] Appl. No.: 34,796

[22] Filed: Apr. 30, 1979

[51] Int. Cl.³ .................. A23J 1/18; C12P 21/00; E21B 43/22; E21B 43/40
[52] U.S. Cl. .................. 166/246; 166/266; 166/268; 426/60; 435/68; 435/170; 435/171; 435/804; 435/923; 435/924; 435/930; 435/938
[58] Field of Search .................. 166/246, 268–274, 166/266; 435/247, 170, 803, 171, 804, 128, 68; 426/60, 62, 69

[56] References Cited

U.S. PATENT DOCUMENTS

| | | | |
|---|---|---|---|
| 2,623,596 | 12/1952 | Whorton et al. | 166/274 |
| 3,065,790 | 11/1962 | Holm | 166/274 |
| 3,193,006 | 7/1965 | Lewis | 166/266 |
| 3,442,332 | 5/1969 | Keith | 166/266 |
| 3,711,372 | 1/1973 | Donnelly | 435/128 |
| 3,844,893 | 10/1974 | Hitzman | 435/247 |
| 3,897,303 | 7/1975 | Sherk et al. | 435/247 |
| 3,982,998 | 9/1976 | Hitzman et al. | 435/246 |
| 4,044,500 | 8/1977 | Hitzman | 47/1.4 |
| 4,145,445 | 3/1979 | Hitzman | 426/60 |

OTHER PUBLICATIONS

Porter, R. E., et al. "The Carbon Dioxide Supply Situation for Miscible Flooding Operations," in *Proceedings, Third ERDA Symposium on Enhanced Oil & Gas Recovery & Improved Drilling Methods*, Petroleum Publishing Co., Tulsa, Ok., vol. 1-Oil, pp. C-5/1 to C-5/10, 1977.
McRee, "CO₂: How it Works, Where it Works," *Petroleum Engineer*, Nov. 1977, pp. 52–63.
Reed et al., *Carbon Dioxide:* in Encyclopedia of Chemical Technology, 2nd Ed., edited by R. E. Kirk and D. F. Othmar, John Wiley and Sons, N.Y., vol. 4, 1964, pp. 353–369.
Stinson, "Methanol Primed for Future Energy Role," *Chem. and Eng. News*, Apr. 2, 1979, pp. 28–30.

Primary Examiner—Stephen J. Novosad

[57] ABSTRACT

A single cell protein plant is operated to produce high density cell growth and a substantially pure stream of generally high pressure carbon dioxide for further use, for example, in enhanced oil recovery operations. The plant employs an air separator producing substantially pure streams of oxygen and nitrogen. The oxygen stream is used to enrich a carrier fluid and used for aeration of the fermenter. The off-gases from the fermenter are separated into a generally high pressure, substantially pure carbon dioxide stream which can be used for enhanced oil recovery and a residual recycle stream to which oxygen is again added and which is returned to the fermenter. The single cell protein is dried and further processed as required for human or animal consumption.

25 Claims, 1 Drawing Figure

ENRICHED OIL RECOVERY USING CARBON DIOXIDE

FIELD OF THE INVENTION

The invention relates to the enhanced recovery of crude oil. In another aspect, the invention relates to the enhanced recovery of crude oil using carbon dioxide, which carbon dioxide is obtained in connection with a process for making single cell protein. In yet another aspect, the invention relates to enhanced recovery of crude oil using nitrogen, which nitrogen is obtained in connection with a process for making single cell protein. In a further aspect, the invention relates to a process for making single cell protein.

BACKGROUND OF THE INVENTION

Enhanced oil recovery processes—thermal, micellar, and miscible or immiscible—are limited by depth, temperature, permeability, temperature, formation parameters, crude composition, fuel source, and many other factors. Carbon dioxide is usually classified as a miscible process but is not limited to such use. Carbon dioxide has been used in enhanced oil recovery operations in many situations: in sandstones, limestones, dolomites, and cherts; to depths of 10,800 feet with no known depth limitation; in formations with permeabilities of less than two millidarcys; at bottom hole temperatures of up to 248 degrees Fahrenheit with no known limitation; in formations varying from 8 feet to 600 feet in thickness and displaying appreciable heterogeneity; where crudes vary in specific gravities from 16 to 45 API; where crudes were displaced immiscibly; for crudes varying in viscosity from 0.3 to 188 centipoise; in reservoirs having oil saturations from 28 to 64 percent; and with well spacing up to over 50 acres per well.

Thus, enhanced recovery of oil using $CO_2$ has been used for extreme ranges in the spectra of preferred criteria, and has been successfully used where other methods were ruled out because of factors such as unfavorable heterogeneity, permeability, oil gravity, and temperature. Although the most widely accepted theory of $CO_2$-enhanced recovery is based on the miscibility of $CO_2$ in crudes, thereby decreasing viscosity, it is also reported that $CO_2$ shows highly efficient immiscible displacement behavior.

The most important problem is finding an economical $CO_2$ source. Current $CO_2$ sources include power plant flue gases, cement plant and limestone plant flue gases, by-product of fertilizer and chemical plants, for example, ammonia plants, naturally occurring gas deposits, and the like. Highly desirable are sources of substantially pure $CO_2$ which are available for direct use in the oil field. Such sources presently available include power plant flue gases after a carbon dioxide recovery step, ammonia plant stack gases, and naturally occurring gas deposits. Carbon dioxide by-product from fermentation industries has also been broadly suggested in the art. However, such sources have been previously rejected because of low availability coupled with high purification costs.

Single cell protein plants are prolific generators of carbon dioxide. However, in the design of single cell protein plants recurrent problems of providing effective gas exchange have been encountered. Briefly, the problems are: (1) to provide an adequate oxygen supply for optimum growth while avoiding oxygen levels which result in oxygen induced cell damage; (2) to adequately distribute the oxygen provided to the ferment; and (3) to maintain adequate flush out rates of carbon dioxide to avoid carbon dioxide inhibition of the ferment.

Accordingly, it is an object of this invention to provide an efficient source of substantially pure carbon dioxide. It is a further object of this invention to provide a method of single cell protein production capable of operating in large-scale under high cell density operations. It is a further object of this invention to operate a single cell protein plant intentionally to produce high pressure, relatively pure carbon dioxide. It is another object to operate such a plant to produce such carbon dioxide for enhanced oil recovery operations. Yet another object is to provide such a fermentation process which reduces compression costs and wastage of purified oxygen. Yet another object is such a process which is simple and well adapted for its intended purpose. Other objects and advantages of the instant invention will be apparent to one skilled in the art from the following description and drawing.

SUMMARY OF THE INVENTION

The use of carbon dioxide for enhanced oil recovery operations in oil fields is well known. Single cell protein plants are known to produce large amounts of carbon dioxide as a by-product of fermentation. The invention comprises modifying and operating a single cell protein plant intentionally to produce generally high pressure relatively pure carbon dioxide for use, for example, in enhanced oil recovery operations. An important feature of the invention is to use an aeration stream enriched with pure oxygen to the fermenter instead of compressed air. When compressed air is used, in practice only about ⅓ of the oxygen supplied can be utilized by the ferment because of mass transfer limitations. By adding, for example, a carbon dioxide stripper to the single cell protein plant, and operating the stripper generally at enhanced pressures, a generally high pressure stream of substantially pure carbon dioxide can be produced. Moreover, since the at least potentially inhibitory carbon dioxide has now been removed, the residual generally high pressure stream can be enriched with oxygen and used again for aeration, thereby reducing compression costs associated with compressed air systems and permitting utilization of substantially all of the purified oxygen further promoting the overall efficiency of the system.

Briefly, my invention comprises using an air separation plant which produces a substantially pure oxygen stream and a substantially pure nitrogen stream. At least a portion of the oxygen stream is mixed with a carrier or flywheel stream, generally at an enhanced pressure, consisting, for example, primarily of oxygen and nitrogen, obtained from a fermenter off-gas separating means operated generally at enhanced pressures. The resulting gaseous-oxygen-enriched mixture forms an aerating stream for feed, generally but not necessarily at an enhanced pressure, to the fermenter. The oxygen and nitrogen content of the aerating stream is regulated by portions of the flywheel stream, the substantially pure oxygen and nitrogen streams from the air separator, and if so desired from an atmospheric air feed stream. An assimilable nitrogen source, an assimilable carbon source, an energy source which generally is also the carbon source, additional nutrients, and an innoculum of a suitable microorganism are also introduced into the fermenter. The concentrations of these media are selected to be effective to permit high cell density growth. Thereafter a high cell density fermentation rate is achieved by regulation of oxygen-enriched air, high stirring rates, and an efficient cooling system, all of which are discussed below. These factors are used to regulate the operation of the fermenter to achieve high cell density operation to achieve design productivity thereby promoting efficiency of the integrated system. The fermenter off-gas separating means also produces a generally high pressure substantially pure stream of carbon dioxide for use, for example, in enhanced oil recovery operations.

BRIEF DESCRIPTION OF THE DRAWING

My invention is illustrated by the attached drawing but should not be limited by or to the drawing. An air separation plant C provides a stream of substantially pure oxygen to a fermenter A where the oxygen is used in a high cell density fermentation process to produce single cell protein and carbon dioxide. The carbon dioxide is removed B from the fermenter off-gas and is employed in enhanced oil recovery operations E to produce oil. The fermenter effluent is dried in a dryer D to produce single cell protein.

DETAILED DESCRIPTION OF THE INVENTION

Figure 1:
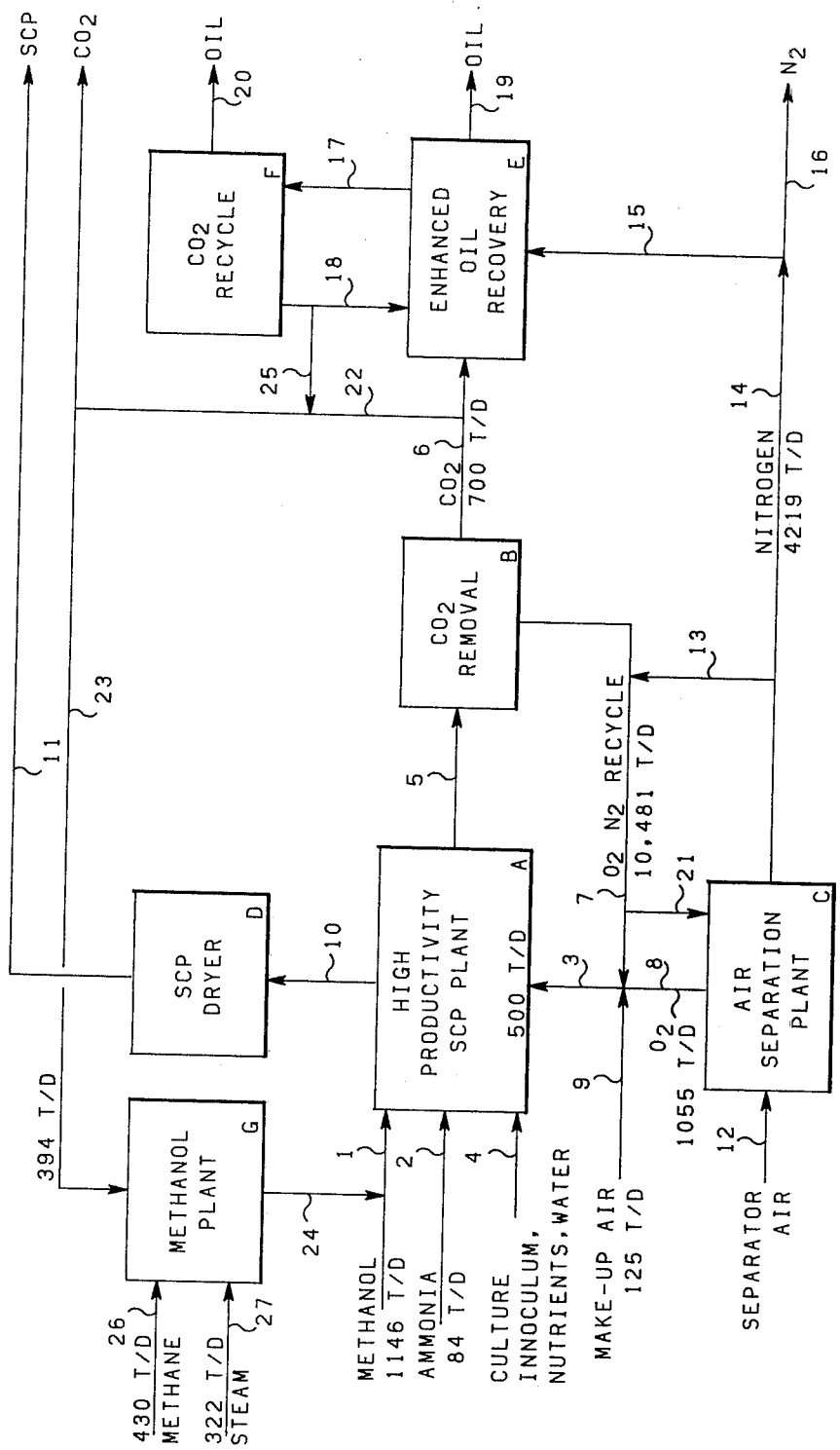

My invention relates to a method for producing substantially pure $CO_2$ from a fermentation process for use in enhanced oil recovery programs which method is highly adapted to oil field utilization. As is known, efforts to relieve world-wide shortages of protein have included production of single cell protein (SCP) by growth of one or another of a variety of microorganisms on various hydrocarbon-containing substrates. The hydrocarbon-containing substrates should be readily available, relatively cheap, uniform, and safe. The use of petroleum hydrocarbons as a carbon energy source has faced practical difficulties in the lack of water solubility and the high consumption of molecular oxygen needed to assist in the microbial conversion. Thus other processes have centered on the use of oxygenated hydrocarbon derivatives of petroleum as feedstocks due to their relatively higher water solubility and consequent adaptability for use in an aqueous fermentation process. These hydrocarbon derivatives can either be provided to the fermentation process in ready made form or the making of the hydrocarbon derivatives can be integrated with fermentation to produce SCP as is disclosed in U.S. Pat. No. 4,145,445. In either event, utilization of petroleum hydrocarbons either directly or after conversion to a water soluble form, for example, methanol, facilitates the development of integrated systems of fermentation processes and oil recovery processes such as the system of the instant invention. Such integrated systems permit significant increases in the overall efficiency of the subsystems involved thereby directly resulting in energy savings and indirectly favoring environmental concerns relating to conservation of earth, air, and water.

Such integrated systems typically require large scale single cell protein plants for efficient operation. In such large scale plants, the various dimensions and operating parameters, e.g., feed rates, productivities and the like, are generally derived by extrapolation from smaller scale prototype fermentation processes. However, it has been found that in most scale-ups, the actual productivity of the large scale plant falls significantly below the values predicted by extrapolation from smaller scale processes. This failure to achieve predicted productivity will become especially significant in high cell density fermentation processes, i.e., those processes resulting in production on a dry weight basis in excess of 100 grams per liter of ferment, where higher viscosities and poor heat transfer properties become increasingly significant as factors tending to hinder optimal oxygen transfer and temperature control.

Nevertheless the high productivities of such high cell density plants are desirable for a number of reasons including savings in space, increases in efficiency, facilitation of direct drying recovery of the SCP product and the like. Moreover such high cell density plants produce an abundance of carbon dioxide which can be readily, efficiently, and economically separated from other fermentation off-gases, such as oxygen and nitrogen, if present, to provide an efficient source of substantially pure carbon dioxide for enhanced oil recovery operations.

I employ in an integrated system for simultaneous production of SCP product and a substantially pure carbon dioxide stream for enhanced oil recovery a high cell density fermenter, an air separation plant, a fermenter off-gas separation means operated generally at enhanced pressures for separating the fermenter off-gas into a generally high pressure substantially pure carbon dioxide stream which can be used, for example, for enhanced oil recovery and a generally high pressure recycle or flywheel stream containing primarily oxygen and nitrogen gases, means for controlling the amount of oxygen in and the rate of aeration supply to the fermenter, and direct drying of the fermenter effluent to produce SCP product.

Referring to the drawing, a carbon and energy source such as a methanol 1, a nitrogen source such as ammonia 2, and an aeration stream containing oxygen 3 are employed in a high productivity SCP plant A which also receives culture innoculum, additional nutrients such as minerals, salts, and vitamins in aqueous solution 4 to produce an SCP effluent stream 10 and an off-gas carbon dioxide-containing stream 5. The off-gases from the fermenter constitute the carbon dioxide-containing stream 5 which is taken to a carbon dioxide stripper B, generally operated at enhanced pressures, for carbon dioxide removal. Separated carbon dioxide provides a generally high pressure substantially pure stream of carbon dioxide 6 for use in enhanced oil recovery E. The carbon dioxide can also be diverted 22 for other uses. A residual gas stream 7 comprising primarily oxygen and/or nitrogen gases is used as a recycle or flywheel stream to provide a carrier fluid for purified oxygen from the oxygen stream 8 from the air separation plant C. Nitrogen losses from the recycle stream can be made up by make-up air 9 or by use of a portion of the substantially pure nitrogen stream 13 from the air separation plant C. Excess pressure or gases in the recycle stream 7 can be bled off to the air separator via bleed-off stream 21 or can be vented to the atmosphere (not shown). The composition of the aerating stream 3 to fermenter A is controlled by controlling streams 7, 8, 9, 13 and 21 to achieve the desired oxygen addition rate and operating pressure of the SCP plant.

From the SCP plant A, the effluent stream 10 containing microorganisms is passed to an SCP dryer D for drying to produce an SCP product stream 11 useful, for example, as a proteinaceous feed supplement for animals or for human beings after further processing, if required.

The air separation plant C receives a separator air stream 12, which can be supplemented by bleed-off stream 21. The air separator stream produces substantially pure streams of oxygen 8 and of nitrogen 14 which can be used in the fermentation process as described above. The nitrogen stream 14 can also be diverted for use as a pusher gas 15 in enhanced oil recovery operations or can be purged 16 for other uses.

Excess carbon dioxide 22 from the $CO_2$ removal step B, if desired, can be combined with production of methanol for use in the SCP plant as described in U.S. Pat. No. 4,145,445 (3/20/79). Such utilization is illustrated by $CO_2$ stream 23 to methanol plant G which in turn provides a methanol product stream 24 to the SCP plant A via stream 1.

The $CO_2$ stream 6 from the $CO_2$ removal step B can be used in enhanced oil recovery E as shown. At least a portion of the carbon dioxide can be recovered from the oil so produced 17 and recycled for reuse in enhanced oil recovery operations 18 as shown. Alternatively, the recovered $CO_2$ can be used in methanol production as shown by stream 25 to methanol plant G via streams 22 and 23. Oil produced from such enhanced oil recovery operations can be taken off in oil product streams 19 and 20.

EXEMPLARY MATERIAL BALANCE

The following overall material balance is intended to be illustrative and to assist one skilled in the art in understanding my invention without limiting the scope thereof.

The relationships calculated are based on stoichiometric relationships. Of course, actual plant calculations will vary, depending, for example, on cell productivities, rate of carbon and energy source consumption, cell yields, and the like. Particular amounts, sizing, and the like can readily be varied for other situations from the descriptions of each step contained in the disclosure of which this material balance is a part.

Methanol, about 1146 tons per day, ammonia, about 84 tons per day, a gas containing 30 weight percent oxygen, about 11,661 tons per day, and culture innoculum, additional nutrients, e.g., minerals, and water, a total of about 1923 tons per day, are employed in the fermentation facility A under aerobic fermentation conditions to produce a single cell protein product (SCP) at the rate of about 500 tons per day on a nominally dry weight basis.

The off-gas stream from the fermenter A is treated in the $CO_2$ stripper B to recover the fermentation-produced carbon dioxide at a rate of about 700 tons per day. The $CO_2$ can be used in oil fields, for example, in a miscible system to reduce oil viscosity and to enhance oil recovery.

The separation of the $CO_2$ from the fermenter off-gas stream leaves a residue gas containing oxygen and nitrogen, about 10,481 tons per day. This oxygen-containing gas is recycled as a flywheel or recycle stream to the fermenter A along with additional oxygen, about 1055 tons per day, from the air separation plant C and make-up air, about 125 tons per day, to compensate for losses of nitrogen. The amounts of the three gas streams is regulated to produce the desired level of oxygen entering the fermenter A. The stream of oxygen-containing gases to the fermenter should be sufficient not only to provide the oxygen necessary for aerobic fermentation conditions, but additionally sufficient to sweep out high contents of $CO_2$ generated by the fermentation which would, unless steadily depleted, tend to inhibit cell growth. The oxygen content and aeration rate is further adjusted so as to prevent oxygen-induced cell damage caused by high partial pressures of $O_2$, i.e., the oxygen content in the aeration stream is selected such that the partial pressure of oxygen therein is less than the partial pressure of oxygen which results in substantial oxygen-induced cell damage. The partial pressure of oxygen which results in substantial oxygen-induced cell damage is defined for this invention as the partial pressure of oxygen greater than that required for optimal growth which results in a diminishment or slowing down of growth.

The air separation plant C produces about 4219 tons per day of nitrogen which can be used as a pusher or drive gas in oil recovery. If desired, a portion of the nitrogen can be utilized in the production of ammonia (not shown).

The stream containing the SCP product, about 3740 tons per day including water and nutrients, is dried in, for example, a spray dryer to produce about 500 tons per day of single cell protein containing about 5 weight percent water.

The carbon dioxide stream 6 can be supplied for enhanced oil recovery operations E. As shown, for purposes of the exemplary material balance, 700 tons per day of substantially pure $CO_2$ are available for enhanced oil recovery procedures. As is known in the art of $CO_2$-enhanced oil recovery, the recovery rate of oil varies from about 1 barrel of oil per 675 cubic feet to about 1 barrel of oil per 2000 cubic feet of carbon dioxide. Hence the exemplary balance of potential enhanced oil recovery ranges between about 6000 and about 17,500 barrels per day without recycling of the $CO_2$. Since it is estimated that about 50% of the $CO_2$ employed in enhanced oil recovery processes can be recovered, the exemplary balance with recycling to enhanced oil recovery ranges between about 9000 and about 26,250 barrels per day.

A portion of the carbon dioxide from streams 6 or 25 can also be used in a methanol producing plant G. The methanol producing plant produces a methanol product stream 24 of 1146 tons per day which is supplied to SCP plant A. Carbon dioxide, about 394 tons per day, methane, about 430 tons per day, and steam about 322 tons per day are supplied to the methanol producing plant G. In addition there is also about 4000 tons of excess nitrogen 14 produced per day which may be used as a pusher gas 15 in enhanced oil recovery operations or may be diverted 16 to other uses.

FERMENTATION PROCESS

The carbon and energy source material of this invention is a substantially methanol-containing stream 1 although any of the lower alcohols of about 1 to 4 carbon atoms per molecule can be present. As is known in the art of methanol production, the methanol produced also may be combined with minor amounts of various materials such as, for example, aldehydes, ketones, acids and ethers. In the present invention it is unnecessary to use substantially pure methanol, since these minor components such as aldehydes, ketones, acids, and ethers are not objectionable for the purposes of carrying out fermentation. The process effluent from an alcohol plant may be used as such. If undesirable amounts of aldehyde are present, ammonia or ammonium compounds, for example, ammonium hydroxide may be added to render harmless the otherwise deleterious amounts of aldehyde materials in the methanol feedstock.

The methanol employed in the fermentation process of the instant invention can be derived from any source. However, advantageous results may be obtained where the methanol producing plant is integrated with the SCP-producing plant as disclosed in U.S. Pat. No. 4,145,445. Integration of such a methanol-producing plant into the instant invention may be accomplished by, for example, using excess recovered $CO_2$ stream 25 from enhanced oil recovery operations in methanol production G for the SCP plant since, as is known in the art of enhanced oil recovery, carbon dioxide is not chemically altered or consumed in such enhanced oil recovery processes. Alternatively, carbon dioxide stream 6 via streams 22 and 23 can be used.

Methanol can be prepared by the catalytic reaction of a lower hydrocarbon, such as natural gas which is predominantly methane, with steam and carbon dioxide. This method is described below.

If the natural gas contains sulfur compounds, treatment by sulfur removal means such as activated carbon beds is desirable, so as to assure that organic sulfur and hydrogen sulfide are adsorbed to avoid possible poisoning of the subsequent catalytic and/or the fermentation processes.

The hydrocarbon gas stream preferably is preheated by heat exchange with hot reformed gas, and mixed with carbon dioxide. Reaction steam such as at about 30 psig is preheated and mixed with the combined hydrocarbon gas/carbon dioxide stream. The mixture then is reformed employing a suitable catalyst such as a nickel catalyst, to produce reformed gases, CO, $CO_2$ and $H_2$. The reformed gases are cooled, as in a waste heat boiler, compressed to a moderately high pressure such as about 4800 psig, and contacted with a suitable catalyst, operating at about 1500 to 9000 psig, preferably about 5000 psig, pressure, and 250° to 400° C. temperature, such as about 300° C., so as to convert the gaseous stream to methanol at least in part. The catalyst most commonly employed is copper mixed with oxides of zinc, chromium, manganese or aluminum. Unreacted gases can be separated and recycled. Typical conversion is of the order of about 12 to 15 percent per pass. The condensed methanol-containing stream is then employed in the fermenter as a carbon and energy source for the microorganisms.

The source of nitrogen for the SCP plant can be any organic or inorganic nitrogen-containing compound known in the art as a suitable source of assimilable nitrogen for metabolic utilization by the organism selected. Suitable organic nitrogen sources include, for example, protein, amino acids, urea, and the like. Suitable inorganic nitrogen sources include, for example, ammonia, ammonium hydroxide, ammonium nitrate, and the like. The presently preferred nitrogen source for the instant invention is ammonia, which may be derived from any suitable source, such as, for example, an ammonia producing plant integrated into a plant for production of SCP as disclosed in U.S. Pat. No. 4,145,445.

The fermentation process is carried out under conditions effective for aerobic microbial fermentation. Exemplary fermentation temperatures are in the range of about 15° C. to about 65° C., with pressures in the range of about 0.1 to 100 atmospheres, more usually about 1 to 30 atmospheres, and more preferably about 3 to 5 atmospheres, since the higher pressures mean a greater level of dissolved oxygen in the aqueous media and usually higher productivities accordingly as well as increasing the efficiency of the integrated system.

A basic feature of the present invention is the ability to control three critical parameters of the fermentation to allow a very high cell density growth even at large scale. The three parameters are (a) oxygen content of the fermenter, (b) amount of stirring, and (c) the amount of cooling available. If any of these factors is inadequate, the very high cell densities of the present invention will not be attained in large scale fermentations and the resulting SCP productivity will be decreased.

The cell densities in the fermentation process of this invention should be broadly from about 110 to about 150 grams (dry basis) per liter of ferment and preferably from about 130 to 150 grams per liter, inasmuch as higher density fermentations produce greater quantities of carbon dioxide. These cell densities are appreciably higher than the cell densities commonly obtained (about 15 to 50 grams per liter).

The oxygen level in the aeration stream to the fermenter should be broadly from about 23 to about 70, preferably from about 23 to about 40 percent by weight. At higher oxygen levels, some microorganisms may be harmed or their growth retarded. The level of oxygen should be controllable and this can be done by regulating the amounts of the makeup air, oxygen from the air separation plant, and the recycle stream from the $CO_2$ stripper. The ability to regulate the oxygen level is important because an oxygen level suitable for small scale fermentation may be inadequate in a large scale fermentation. In that case, the oxygen level could be increased to provide the expected productivity. The oxygen level in the gas stream entering the fermenter can be determined by commercially available oxygen analyzers.

The stirring in the fermenter must be sufficient to provide effective mixing of the fermenter broth at the high cell densities desired. Any type of stirrer, including flat plate and shrouded turbines, that provide good mixing can be used. However, in all cases, it is required that power be present to provide from about 4 to about 12 horsepower per cubic meter of broth in fermenter to overcome the high broth viscosity.

Since the aerobic fermentation evolves a considerable amount of heat, it is essential that sufficient cooling be present to maintain the desired fermenter temperature. A cooling system with a surface area of from about 3 to about 8 square meters per cubic meter of broth in fermenter is preferred. Cooling surface areas below that range are inadequate for the necessary cooling and those above that range exceed what is required. The cooling fluid can be any suitable liquid such as ammonia, mixtures of water and ethylene glycol, and the like. The cooling fluid should be capable of being serviceable in the operating range of about $-15°$ C. and about $+10°$ C. Below about $-15°$ C., ice crystals have been found to form on the surface of the cooling means.

Sufficient water is maintained in the fermentation means so as to provide for the particular requirements of the microorganisms employed. Generally, in the process, any microorganisms capable of utilizing a methanol-containing feedstock in aqueous media can be utilized. Among the microorganisms suitable for the types of fermentation described are the bacteria, yeasts, and fungi, such as from the following genera:

Bacteria: Bacillus, Pseudomonas, Protaminobacter, Micrococcus, Arthrobacter, Corynebacterium, Methanomonas, Methylococcus, Methylomonas, Methylobacter, Methylosinus, Methylocystis, Curtobacterium, Acinebacter, Brevibacterium, Nocardia, Mycobacterium, Streptomyces, and Actinomyces.

Yeasts: Candida, Hansenula, Torulopsis, Pichia, Saccharomyces, Rhodotorula, Brettanomyces, and Debaryomyces.

Fungi: Aspergillus, Monilia, Rhizopus, Penicillium, Fusarium, Mucor, Alternaria, Hyphomicrobium, and Helminthosporium.

It is currently preferred that yeasts of the genera Candida, Hansenula, Torulopsis, Pichia, and Saccharomyces be utilized in the process of this invention. Examples of suitable species include:

| | |
|---|---|
| *Brettanomyces petrophilium* | *Pichia farinosa* |
| *Candida biodinii* | *Pichia polymorpha* |
| *Candida lipolytica* | *Pichia membranaefaciens* |
| *Candida mycoderma* | *Pichia pinus* |
| *Candida utilis* | *Pichia pastoris* |
| *Candida stellatoidea* | *Pichia trehalophila* |
| *Candida robusta* | *Saccharomyces cerevisiae* |
| *Candida claussenii* | *Saccharomyces fragilis* |
| *Candida rugosa* | *Saccharomyces rosei* |
| *Candida tropicalis* | *Saccharomyces acidifaciens* |
| *Debaryomyces hansenii* | *Saccharomyces elegans* |
| *Hansenula minuta* | *Saccharomyces rouxii* |
| *Hansenula saturnus* | *Saccharomyces lactis* |
| *Hansenula californica* | *Torulopsis sonorensis* |
| *Hansenula mrakii* | *Torulopsis candida* |
| *Hansenula silvicola* | *Torulopsis bolmii* |
| *Hansenula polymorpha* | *Torulopsis versatilis* |
| *Hansenula wickerhamii* | *Torulopsis glabrata* |
| *Hansenula capsulata* | *Torulopsis molishiana* |
| *Hansenula glucozyma* | *Torulopsis nemodendra* |
| *Hansenula henricii* | *Torulopsis nitratophila*, and |
| *Hansenula nonfermentans* | *Torulopsis pinus* |
| *Hansenula philodendra* | |

Presently preferred microorganisms include *Pichia pastoris* which has been assigned the numerical designation NRRL Y-11430 by the United States Department of Agriculture, Agricultural Research Service, Northern Regional Research Laboratories of Peoria, Ill; *Pichia pastoris* NRRL Y-11431, and *Hansenula polymorpha* NRRL Y-11170. These strains have been found particularly suitable for use in producing SCP protein materials at high cell densities with high yields and grow suitably on oxygenated hydrocarbon feedstocks, particularly a lower alcohol such as methanol.

Suitable minerals, growth factors, vitamins and the like generally are added in amounts sufficient to provide for the particular needs of the microorganisms utilized. Minerals and growth factors, and the like, for the microorganisms which are employed vary according to the particular requirements of the microorganisms and are generally known to those skilled in the art or are readily determined by those so skilled.

The mineral salts medium employed can be selected from such media as are known in the art depending on the particular microorganism employed. Typically, a suitable medium, FM-12, would include the following:

| One Liter Aqueous Solution | |
|---|---|
| Component | Amount |
| $H_3PO_4$ (85%) | 2.0 ml |
| KCl | 1.0 g |
| $MgSO_4 \cdot 7H_2O$ | 1.5 g |
| $CaCl_2 \cdot 2H_2O$ | 0.2 g |

| -continued | |
|---|---|
| One Liter Aqueous Solution | |
| Component | Amount |
| NaCl | 0.1 g |
| Trace mineral solution | 5.0 ml |

The trace mineral solution is formulated according to the following recipe:

| One Liter Aqueous Solution | |
|---|---|
| Component | Amount |
| $CuSO_4 \cdot 5H_2O$ | 0.06 g |
| KI | 0.08 g |
| $FeCl_3 \cdot 6H_2O$ | 4.80 g |
| $MnSO_4 \cdot H_2O$ | 0.30 g |
| $Na_2MoO_4 \cdot 2H_2O$ | 0.20 g |
| $ZnSO_4 \cdot 7H_2O$ | 2.00 g |
| $H_3BO_3$ | 0.02 g |

Where desired, input streams to the fermenter can be combined, such as combining the methanol feed with the mineral salts medium. As an optional feature, the fermenter could be fed preferably continuously a mineral salts medium as described above further containing a high concentration of methanol of at least 20 percent, which will sterilize the mineral medium and avoid the necessity of separate sterilization, and at the same time provide convenient means of feeding methanol as the carbon and energy source material.

By maintaining a high input of methanol and proper control of fermentation pressure, control, input of components, and aeration stream input rate and oxygen content as herein described, it is feasible to obtain very high cell densities, for example, in the range from about 110 to about 150 grams of SCP on a dry weight basis per liter of ferment. Such very high cell densities are desirable for efficiency, to have minimum liquid be handled in the fermenter effluent, thus eliminating the need for centrifugation in the formation of an SCP product and routine use of waste treatment ponds and the like.

$CO_2$ STRIPPER

The off-gas stream from the fermenter, containing carbon dioxide, oxygen, nitrogen, water, and trace gases, is taken to a $CO_2$ stripper, generally operated at enhanced pressure, where carbon dioxide is removed from the off-gas stream, for example, by an absorption processes utilizing a selective absorbent such as, for example, monoethanolamine or diethanolamine as are known in the art. By operating the $CO_2$ stripper near fermentation pressure, recompression expenses are minimized for the flywheel or recycle stream and a high pressure substantially pure $CO_2$ product stream is produced. The thus recovered $CO_2$ then is employed at least in part in enhanced oil recovery procedures as hereinafter described. In an integrated system for SCP production as described in U.S. Pat. No. 4,145,455, the $CO_2$ can also be used in methanol synthesis. Alternatively and preferably, the recovered $CO_2$ from enhanced oil recovery operations can be so employed.

After removal of the carbon dioxide, the residual gas stream comprising primarily oxygen and nitrogen is recycled for use as a flywheel carrier fluid to carry the oxygen from the air separator through the fermentation process at the enhanced pressures, preferably in the range of from 3 to 5 atmospheres, used in this invention. Pressure losses in the flywheel stream can be made up by compression means, for example, a blower (not shown) in recycle stream 7. Nitrogen losses from the flywheel carrier fluid can be compensated for by make-up air such as atmospheric air or by use of a portion of the substantially pure nitrogen stream from the air separator. Excess nitrogen bleed-off means and pressure control means are also provided. Use of such a flywheel carrier fluid increases the efficiency of the present invention by eliminating the need to compress anew the entire volume of the aeration stream during each cycle through the fermenter. In effect, only the aeration stream regeneration streams, i.e., the oxygen stream, make-up air stream and make-up nitrogen stream need be pressurized. The oxygen is recycled to obtain complete utilization of the oxygen.

AIR SEPARATION

Relatively pure oxygen and nitrogen can be produced by compressing air, optionally with recycle stream gas 7 via 21 from the $CO_2$ stripper, to such as about 4 to 5 atmospheres, and any carbon dioxide and other acidic gases thus present removed by scrubbing with such as a potassium hydroxide solution. The compressed, scrubbed air then can be further compressed to such as about 200 atmospheres, with such cooling as is suitable, and any moisture condensing is removed. The compressed air then is scrubbed by treatment with such as solid KOH or activated alumina. The gas from the last compression stage, such as at 170° C. and 200 atmospheres, is further cooled to about −30° C. by suitable cooling means, and then subjected to liquefaction/separation as is known in the art to produce, as separate streams, a nitrogen stream containing about 98 weight percent nitrogen by weight and 2 weight percent oxygen by weight and a liquid oxygen stream of about 99 weight percent oxygen and 1 weight percent nitrogen, typically. The oxygen stream is passed to the fermenter and the nitrogen stream can be used as a pusher gas in oil production or as a starting material in an ammonia plant.

DRYER

The entire fermenter effluent is preferably directly dried using spray dryers, drum dryers and the like without the need for a centrifugation step. The direct drying is possible as a result of the high cell densities in the fermenter. At lower cell densities, the large quantities of water that must be removed makes direct drying uneconomical and a concentration step is normally employed. The use of direct drying provides significant economic and environmental advantages to the present invention. In a large scale fermentation plant, a significant capital investment in centrifuges is avoided. In addition, problems of maintaining sterile conditions in the centrifuges and in any recycle fluids are avoided. Since there is no waste associated with this process, there is no need for waste treatment facilities.

The microorganisms in the fermenter effluent can be killed and rendered suitable for feeding by heating to pasteurization temperatures, either before or after the drying step. Although the pasteurization conditions vary considerably, depending in part on the microorganism, a typical set of pasteurization conditions suitable for use with some microorganisms is about 100° C. for about 30 seconds.

The fermenter effluent contains various fats, carbohydrates, sugars, various salts, vitamins, growth factors, and the like, as well as the protein which is most desired. All of the components of the fermenter effluent are desirable in animal nutrition, and so can become an integral part of the animal feed supplement. This avoids wastage of water-soluble products, proteinaceous materials, nutrients, and the like, which would be lost if only the cellular material was separated out, such as by filtration and the like, and utilized. The salt content of the fermenter effluent will vary depending on the level of salts maintained for growth purposes. The salts balance analysis of the fermenter effluent would be expected to be close to that of the salts balance of the salts feed to the fermenter.

ENHANCED OIL RECOVERY

The carbon dioxide stream 6 from the $CO_2$ stripper can be used in any of the methods of $CO_2$-mediated enhanced oil recovery such as are known in the art. For example, the carbon dioxide can be liquefied and employed in the fracturing and acidizing treatment of oil and gas wells. Preferably, however, the thus-produced carbon dioxide is employed in a miscible-process enhanced oil recovery process such as, for illustrative purposes, carbon dioxide miscible flooding.

Preferred criteria have been established in the art of $CO_2$ miscible flooding:

| Criteria | Value |
| --- | --- |
| Depth (feet) | 2000+ |
| Thickness (feet) | Not critical |
| Permeability (millidarcies) | 5+ |
| Homogeneity | Good |
| Oil Saturation (%) | 25+ |
| Oil viscosity (centipoises) | 5− |
| Oil Gravity (degrees API) | 35+ |
| Gas Cap | Not critical (unless relatively large) |
| Bottom Water | Not critical |
| Temperature | Not critical |

However, many situations are known where $CO_2$-mediated enhanced oil recovery procedures have been effectively used outside the range of preferred criteria shown and the invention is not to be limited thereby.

$CO_2$-miscible flooding can be used either where communication between adjacent wells has been established or where it has not been established. In the first situation, the carbon dioxide is injected into an injector well and oil is removed from a recovery well. Most $CO_2$ floods have been water-injected, i.e., alternating slugs of $CO_2$ and water are injected wherein the water serves to maintain the desired $CO_2$ injection pressure. Carbonated water has been ineffective because $CO_2$ dissolved in water must be transferred from water to oil by diffusion and mobilize connate water ahead of it. Upon initial injection it is believed that the carbon dioxide is not miscible in the oil. However, carbon dioxide has the ability to vaporize hydrocarbon components of the oil, thereby forming a miscible mixture between the reservoir oil and the injected carbon dioxide. The dissolved carbon dioxide volumetrically expands the oil and reduces its viscosity, allowing the oil to flow more readily and resulting in greater recovery. The carbon dioxide can also be used as a pusher gas to drive the lowered viscosity oil toward production wells. Alternatively, the excess nitrogen gas 15 can be used as such a pusher gas.

Carbon dioxide can also be effectively utilized in the second situation where the same well is cycled over an injection period and a production period, the so-called huff and puff injection method. In this procedure, the gaseous carbon dioxide is injected, preferably at an elevated temperature to facilitate dissolving the carbon dioxide into the oil, into the formation until the formation immediately adjacent the well bore has become substantially saturated with carbon dioxide as evidenced by the attaining of a substantially constant pressure.

The well is then operated as a producer. The carbon dioxide pressure in the formation drives a stream comprising lowered-viscosity oil, water, and free $CO_2$ into the well bore and out of the well. The production period of the huff and puff cycle can be continued until the formation pressure drops to zero, although preferably some of the injected $CO_2$ will be left in the formation to facilitate movement of formation oil into the depletion zone resulting from the production period of the cycle to actuate in time the entire reservoir served by the wells or break through to an adjacent well. After the $CO_2$ pressure in the formation has fallen to a preselected value, the injection period of the cycle is recommenced.

The solution stream 17 of oil and carbon dioxide produced from production well or from a well during, for example, the production portion of a huff and puff cycle is taken to a $CO_2$ recycle operation wherein the dissolved $CO_2$ is removed from the crude oil, for example, by heating to vaporize substantially all of the dissolved $CO_2$. The separated crude oil constitutes oil product stream 20. The recovered $CO_2$ stream 18 can then be recycled through additional enhanced oil recovery operations. Alternatively, a portion of the carbon dioxide can be diverted via stream 23 for other uses, for example, utilization in a methanol production step in an integrated system of SCP production and crude oil recovery.

The disclosure, including exemplary data, illustrates the value and effectiveness of my invention. The examples, the knowledge and background of the field of my invention, and general principles of the biological, chemical, and other applicable sources, form the bases from which the broad descriptions of the invention, including the ranges of conditions and generic groups of operant components have been developed which in turn form the bases for my claims here appended.

I claim:

1. A method for enhanced oil recovery comprising in combination:
    (a) producing a single cell protein material by culturing under aqueous aerobic fermentation conditions at a pressure in the range from about 0.1 to about 100 atmospheres at least one microorganism species capable of using a methanol containing feedstock in aqueous media in an aqueous ferment employing effective amounts of a substantially methanol containing feedstream as a carbon and energy substrate, assimilable nitrogen, and feeding an aqueous mineral salts medium to the ferment and recovering the resulting microorganisms as a single cell protein material, further including
    (aa) providing oxygen-enriched fluid further comprising nitrogen, stirring and controlling fermentation temperature to maintain efficient cell growth;
    (bb) separating fermenter off-gases into a substantially pure carbon dioxide stream and a recycle stream comprising oxygen and nitrogen; and
    (cc) continuously enriching said recycle stream with oxygen and adding the resulting oxygen-enriched fluid stream to the fermenter to utilize substantially all of the oxygen during fermentation; and
    (b) injecting at least a portion of said substantially pure carbon dioxide stream into an underground formation containing crude oil at an effective pressure and rate to effect enhanced crude oil production from said formation; and
    (c) withdrawing said crude oil from said formation at a higher rate of production as compared to the rate before injecting substantially pure carbon dioxide into the underground formation.

2. A method as in claim 1 wherein:
    (a) said carbon dioxide is utilized in a miscible process wherein said substantially pure carbon dioxide is injected into an underground formation containing crude oil at an effective pressure and in an amount sufficient to saturate said crude oil at the partial pressures of carbon dioxide penetrating through said formation and thereby form a solution of said carbon dioxide in said crude oil, solution having a reduced viscosity relative to the viscosity of said crude oil.

3. A method as in claim 2 further comprising:
    (a) separating said solution of carbon dioxide in crude oil into a recycle carbon dioxide stream and a crude oil product stream.

4. A method as in claim 3 wherein:
    (a) at least a portion of said substantially pure carbon dioxide stream is used in the synthesis of a methanol feed for use as said carbon and energy source.

5. A method as in claim 3 wherein:
    (a) at least a portion of said recycle carbon dioxide stream is used in the synthesis of a methanol feed for use as said carbon and energy source.

6. A method as in claim 1 wherein step (aa) of claim 1 further comprises:
    (a) separating an oxygen and nitrogen containing stream into a substantially pure oxygen stream and a substantially pure nitrogen stream; and
    (b) using at least a portion of said substantially pure oxygen stream to form said oxygen-enriched fluid.

7. A method as in claim 1 wherein:
    (a) step (bb) is conducted at a first preselected enhanced pressure to produce a high pressure substantially pure carbon dioxide stream and a high pressure recycle stream.

8. A method as in claim 7 wherein:
    (a) said recycle stream and said oxygen-enriched fluid stream are maintained at a pressure approximately equal to the first preselected enhanced pressure.

9. A method as in claim 8 wherein:
    (a) said preselected pressure is in the range from at least above 1 to about 30 atmospheres.

10. A method as in claim 8 wherein:
    (a) said preselected pressure is in the range from at least above 1 to about 5 atmospheres.

11. A method as in claim 8 wherein:
    (a) said preselected pressure is in the range of from about 3 to about 5 atmospheres.

12. A method as in claim 8 further comprising:
    (a) separating atmospheric air into a substantially pure oxygen stream and a substantially pure nitrogen stream; and
    (b) maintaining the oxygen content of said oxygen enriched fluid stream at a preselected level by pressurizing to said first preselected pressure at least a portion of said substantially pure oxygen stream and mixing it with said oxygen enriched fluid stream.

13. A method as in claim 12 further comprising:
(a) maintaining the nitrogen content of said oxygen enriched fluid stream at a preselected level by pressurizing to said first preselected level at least a portion of said substantially pure nitrogen stream and mixing it with said oxygen enriched fluid stream.

14. A method as in claim 12 further comprising:
(a) maintaining the nitrogen content of said oxygen enriched fluid stream by pressurizing atmospheric air to said first preselected pressure and mixing with said oxygen enriched fluid stream.

15. A method as in claim 12 wherein:
(a) said preselected level of said oxygen content of said oxygen enriched fluid stream is determined such that the partial pressure of oxygen therein is less than the partial pressure of oxygen which results in substantial oxygen-induced cell damage.

16. A method as in claim 15 wherein:
(a) said oxygen enriched fluid stream is passed through the fermenter at a rate and with stirring effective
   (aa) to prevent oxygen deficiency from limiting the rate of growth of said culture; and
   (bb) to prevent carbon dioxide excess from limiting growth of said culture.

17. A method as in claim 6 wherein:
(a) said microorganism is selected from the genera Candida, Hansenula, Torulopsis, Saccharomyces, Pichia, Debaryomyces, and Brettanomyces.

18. The method as in claim 17 wherein:
(a) said microorganism is selected from the species

| | |
|---|---|
| Brettanomyces petrophilium | Pichia farinosa |
| Candida biodinii | Pichia polymorpha |
| Candida lipolytica | Pichia membranaefaciens |
| Candida mycoderma | Pichia pinus |
| Candida utilis | Pichia pastoris |
| Candida stellatoidea | Pichia trehalophila |
| Candida robusta | Saccharomyces cerevisiae |
| Candida claussenii | Saccharomyces fragilis |
| Candida rugosa | Saccharomyces rosei |
| Candida tropicalis | Saccharomyces acidifaciens |
| Debaryomyces hansenii | Saccharomyces elegans |
| Hansenula minuta | Saccharomyces rouxii |
| Hansenula saturnus | Saccharomyces lactis |
| Hansenula californica | Torulopsis sonorensis |
| Hansenula mrakii | Torulopsis candida |
| Hansenula silvicola | Torulopsis bolmii |
| Hansenula polymorpha | Torulopsis versatilis |
| Hansenula wickerhamii | Torulopsis glabrata |
| Hansenula capsulata | Torulopsis molishiana |
| Hansenula glucozyma | Torulopsis nemodendra |
| Hansenula henricii | Torulopsis nitratophila, and |
| Hansenula nonfermentans | Torulopsis pinus |
| Hansenula philodendra | |

19. A method as in claim 17 wherein:
(a) said microorganism is selected from the genera Candida, Hansenula, Torulopsis, Pichia, and Saccharomyces.

20. A method as in claim 17 wherein:
(a) said carbon and energy source material is an alcohol of 1 to 4 carbon atoms.

21. A method as in claim 20 wherein:
(a) said alcohol is methanol.

22. A method as in claim 6 or 12 wherein:
(a) said substantially pure nitrogen stream is used in enhanced oil recovery.

23. A method as in claim 1 wherein step (aa) further includes:
(a) maintaining efficient cell growth at a cell density of at least about 110 to 150 grams, on a dry weight basis, per liter of ferment.

24. A method as in claim 1 wherein step (aa) further includes:
(a) maintaining efficient cell growth at a cell density of at least about 130 to 150 grams, on a dry weight basis, per liter of ferment.

25. A method for enhanced oil recovery comprising in combination:
(a) producing a single cell protein material by culturing under aqueous aerobic fermentation conditions at least one microorganism species in an aqueous ferment employing effective amounts of carbon and energy substrate, assimilable nitrogen, and feeding an aqueous mineral salts medium to the ferment, and recovering the resulting microorganisms as a single cell protein material, further including
   (aa) separating an oxygen and nitrogen containing stream into a substantially pure oxygen stream and a substantially pure nitrogen stream;
   (bb) using at least a portion of said substantially pure oxygen stream to form an oxygen-enriched fluid further comprising nitrogen;
   (cc) maintaining the nitrogen content of the oxygen-enriched fluid at a preselected level;
   (dd) providing the oxygen-enriched fluid, stirring, and controlling fermentation temperature to maintain efficient cell growth;
   (ee) separating fermenter off-gases into a substantially pure carbon dioxide stream and a recycle stream comprising oxygen and nitrogen; and
   (ff) continuously enriching said recycle stream with oxygen and adding the resulting oxygen-enriched fluid stream to the fermenter to utilize substantially all of the oxygen during fermentation; and
(b) injecting at least a portion of said substantially pure carbon dioxide stream into an underground formation containing crude oil at an effective pressure and rate to effect enhanced crude oil production from said formation; and
(c) withdrawing said crude oil from said formation at a higher rate of production as compared to the rate before injecting substantially pure carbon dioxide into the underground formation.

* * * * *

UNITED STATES PATENT AND TRADEMARK OFFICE
CERTIFICATE OF CORRECTION

PATENT NO. : 4,261,420

DATED : April 14, 1981

INVENTOR(S) : Donald O. Hitzman

It is certified that error appears in the above–identified patent and that said Letters Patent are hereby corrected as shown below:

Column 14, line 22, delete "said", second occurrence; line 23, delete "said" before "crude" and insert --- said --- before "solution".
Column 15, line 32, delete "6" and substitute --- 16 ---.

Signed and Sealed this

Twenty-first Day of July 1981

[SEAL]

Attest:

GERALD J. MOSSINGHOFF

Attesting Officer        Commissioner of Patents and Trademarks